United States Patent
Hood, Jr. et al.

(10) Patent No.: US 9,309,168 B2
(45) Date of Patent: Apr. 12, 2016

(54) STAGED PROPYLENE PRODUCTION PROCESS

(71) Applicants: Allen David Hood, Jr., Houston, TX (US); Robert S. Bridges, Friendswood, TX (US)

(72) Inventors: Allen David Hood, Jr., Houston, TX (US); Robert S. Bridges, Friendswood, TX (US)

(73) Assignees: Equistar Chemicals, LP, Houston, TX (US); Lyondell Chemical Technology, L.P., Houston, TX (US)

( * ) Notice: Subject to any disclaimer, the term of this patent is extended or adjusted under 35 U.S.C. 154(b) by 58 days.

(21) Appl. No.: 13/738,631

(22) Filed: Jan. 10, 2013

(65) Prior Publication Data
US 2014/0194659 A1 Jul. 10, 2014

(51) Int. Cl.
*C07C 6/04* (2006.01)
*C07C 6/02* (2006.01)
*C07C 4/06* (2006.01)

(52) U.S. Cl.
CPC .... *C07C 4/06* (2013.01); *C07C 6/04* (2013.01)

(58) Field of Classification Search
CPC .................................. C07C 6/02; C07C 6/04
USPC .......................... 585/312–316, 324, 643–647
See application file for complete search history.

(56) References Cited

U.S. PATENT DOCUMENTS

| | | | |
|---|---|---|---|
| 5,853,551 A | 12/1998 | Boucot et al. | |
| 6,646,172 B1 * | 11/2003 | Schwab et al. | 585/324 |
| 7,214,841 B2 * | 5/2007 | Gartside et al. | 585/324 |
| 2006/0089517 A1 | 4/2006 | Podrebarac et al. | |
| 2006/0161033 A1 | 7/2006 | Chodorge et al. | |
| 2008/0146856 A1 | 6/2008 | Leyshon | |
| 2012/0095275 A1 | 4/2012 | Coleman et al. | |

OTHER PUBLICATIONS

The International Search Report and Written Opinion for PCT/US2014/010673 mailed Apr. 28, 2014.

* cited by examiner

*Primary Examiner* — In Suk Bullock
*Assistant Examiner* — Youngsul Jeong

(57) ABSTRACT

Processes for forming propylene are described herein. The processes generally include reacting a metathesis feed stream including butene with ethylene in the presence of a first metathesis catalyst via a first metathesis reaction to form a first metathesis product stream including propylene, ethylene, butene, and $C_{5+}$ olefins; separating at least a portion of the propylene and ethylene from the first metathesis product stream to form a first overhead stream and to form a first de-propenized bottoms stream including butene and $C_{5+}$ olefins; reacting at least a portion of the first de-propenized bottoms stream with ethylene in the presence of a second metathesis catalyst via a second metathesis reaction to form a second metathesis product stream including propylene, ethylene, butene, and $C_{5+}$ olefins; and separating at least a portion of the propylene and ethylene from the second metathesis product stream to form a second overhead stream; and recovering propylene from the first overhead stream, the second overhead stream or combinations thereof.

14 Claims, 1 Drawing Sheet

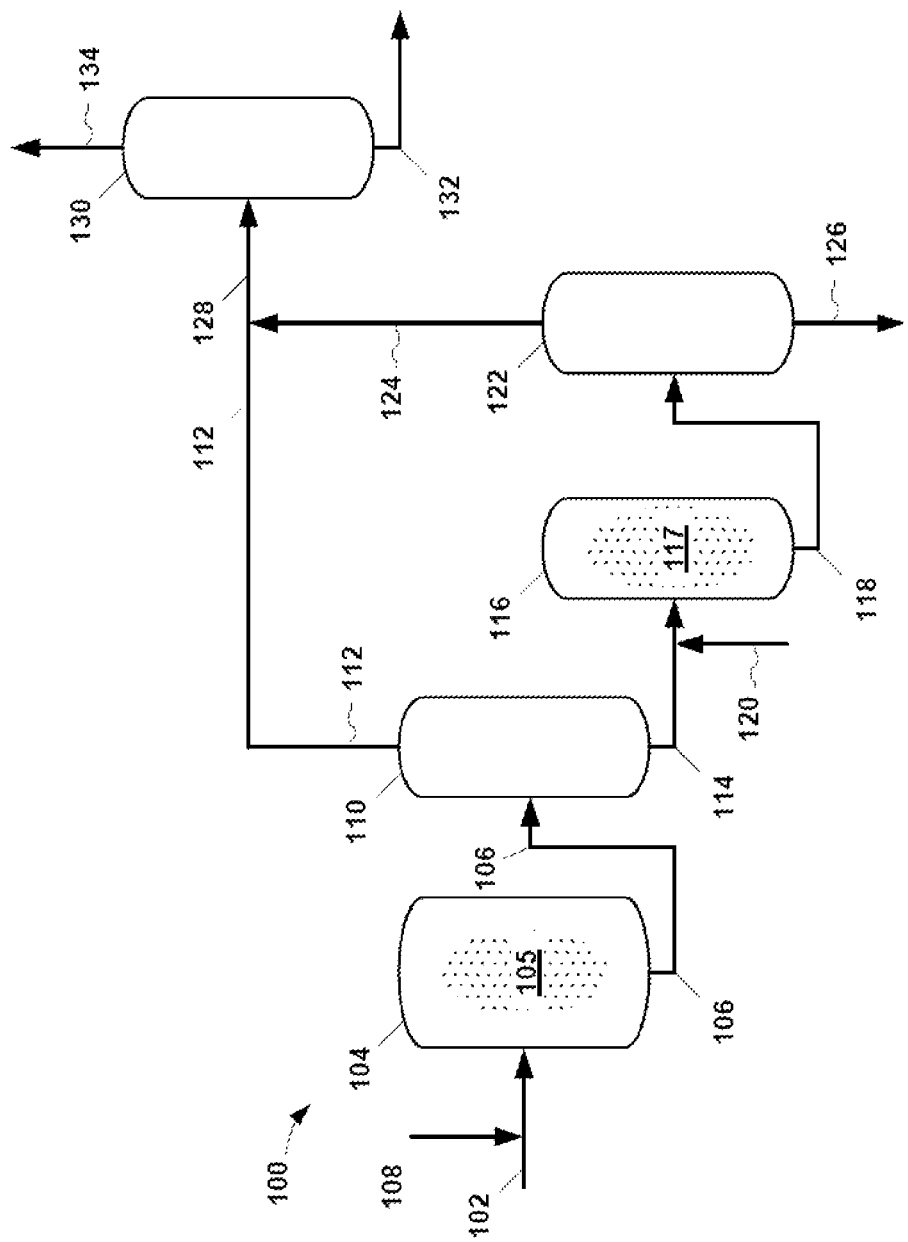

STAGED PROPYLENE PRODUCTION PROCESS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

1. Field of the Invention

The present invention generally relates to propylene production processes. More particularly, the present invention relates to propylene production processes including staged metathesis reactions.

2. Related Art

This section introduces information from the art that may be related to or provide context for some aspects of the techniques described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

Propylene can be produced by the metathesis reaction of linear butene (n-butene) with ethylene. However, conversion rates of the butene to propylene are often limited by a variety of factors, including limited recycle rates, for example.

The present invention is directed to resolving, or at least reducing, one or all of the problems mentioned above.

SUMMARY

Various embodiments of the present invention include processes for forming propylene. The processes generally include reacting a metathesis feed stream including butene with ethylene in the presence of a first metathesis catalyst via a first metathesis reaction to form a first metathesis product stream including propylene, ethylene, butene, and $C_{5+}$ olefins; separating at least a portion of the propylene and ethylene from the first metathesis product stream to form a first overhead stream and to form a first de-propenized bottoms stream including butene and $C_5+$ olefins; reacting at least a portion of the first de-propenized bottoms stream with ethylene in the presence of a second metathesis catalyst via a second metathesis reaction to form a second metathesis product stream including propylene, ethylene, butene, and $C_{5+}$ olefins; and separating at least a portion of the propylene and ethylene from the second metathesis product stream to form a second overhead stream; and recovering propylene from the first overhead stream, the second overhead stream or combinations thereof.

One or more embodiments include the process of the preceding paragraph, wherein the first overhead stream includes propylene and ethylene and the second overhead stream includes propylene and ethylene.

One or more embodiments include the process of any preceding paragraph, wherein the process further includes separating at least a portion of the first overhead stream to form an ethylene stream and a propylene stream.

One or more embodiments include the process of any preceding paragraph, wherein the process further includes separating at least a portion of the second overhead stream to form an ethylene stream and a propylene stream.

One or more embodiments include the process of any preceding paragraph, wherein the process further includes separating at least a portion of the first overhead stream and at least a portion of the second overhead stream to form an ethylene stream and a propylene stream.

One or more embodiments include the process of the preceding paragraph, wherein the process further includes recycling at least a portion of the ethylene stream to the first metathesis reaction, the second metathesis reaction or a combination thereof.

One or more embodiments include the process of any preceding paragraph, wherein the metathesis feed stream further comprises Raffinate-2.

One or more embodiments include the process of any preceding paragraph, wherein the first metathesis reaction, the second metathesis reaction or a combination thereof further include reacting the corresponding metathesis feed stream with ethylene in the presence of an isomerization catalyst.

One or more embodiments include the process of any preceding paragraph, wherein the isomerization catalyst includes magnesium oxide.

One or more embodiments include the process of any preceding paragraph, wherein ethylene is introduced to the first metathesis reaction and the second metathesis reaction at rates sufficient to provide a lower ethylene:butene ratio contacting the first metathesis catalyst than the ethylene:butene ratio contacting the second metathesis catalyst.

One or more embodiments include the process of any preceding paragraph, wherein the first metathesis reaction takes place at an first ethylene:butene ratio of from 0.3:1 to 3:1.

One or more embodiments include the process of any preceding paragraph, wherein the second metathesis reaction takes place at a second ethylene:butene ratio of from 2.0:1 to 10:1.

One or more embodiments include the process of any preceding paragraph, wherein the process exhibits a total butene conversion of at least 85%.

One or more embodiments include the process of any preceding paragraph, wherein the first metathesis catalyst and the second metathesis catalyst include a transition metal oxide.

One or more embodiments include the process of any preceding paragraph, wherein the first metathesis catalyst and second metathesis catalyst include the same material.

One or more embodiments include the process of any preceding paragraph, wherein separating at least a portion of the propylene and ethylene from the second metathesis product forms a second de-propenized bottoms stream including butene and $C_{5+}$ olefins.

One or more embodiments include a process for producing propylene including sequentially reacting a metathesis feed stream including butene with ethylene in the presence of a metathesis catalyst to form propylene.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF DRAWINGS

The claimed subject matter may be understood by reference to the following description taken in conjunction with the accompanying drawings, in which like reference numerals identify like elements, and in which:

FIG. 1 illustrates an embodiment of a propylene production process utilizing sequential metathesis reactions.

While the invention is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

In the description below, unless otherwise specified, all compounds described herein may be substituted or unsubstituted and the listing of compounds includes derivatives thereof. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Embodiments described herein include processes for forming propylene. The processes generally include sequentially reacting a metathesis feed stream including butene with ethylene in the presence of a metathesis catalyst to form propylene.

The butene/metathesis feed stream may be supplied by any known source. However, in one or more embodiments, the butene/metathesis feed stream is supplied from Raffinate-2. Raffinate-1 is generally a co-product of a butadiene extraction process unit and is the balance of $C_4$ butadiene concentrates after separation of butadiene by a solvent process, such as extraction or extractive distillation, for example. Raffinate-1 includes predominantly $C_4$ mono-olefins and $C_4$ paraffins. The stream is sometimes referred to as mixed butylenes because the composition may include about 75 wt. % $C_4$ mono-olefins, for example. The saturated hydrocarbons in Raffinate-1 generally include iso- and normal-butane. The mono-olefin content varies depending on the feedstock of the ethylene process unit that produced the $C_4$ butadiene concentrate.

Raffinate-1 may be further processed to remove the isobutylene. This can be accomplished in a two-step process by reaction with water to make tertiary-butyl alcohol or with methanol to produce methyl-tertiary-butyl-ether, which can then be re-cracked to high purity isobutylene, for example. Raffinate-1, after removal of the isobutylene, is referred to as Raffinate-2, which includes predominantly 1-butene, 2-butene and butanes.

Alternatively, the metathesis feed stream may be formed by contacting a first feed stream including ethylene with a dimerization catalyst to form a dimerization product stream including n-butene. As used herein, the term "dimerization" refers to a chemical reaction in which two identical molecular entities react to form a single dimer. In the present embodiments, the identical molecular entities are generally ethylene, while the dimer is generally butene.

The dimerization catalyst may include catalyst known in the art to be capable of converting ethylene to linear $C_4$ olefins (i.e., n-butene) upon reaction. For example, dimerization catalysts may include homogenous catalyst compounds including nickel. Many catalysts containing nickel are known to dimerize ethylene to butene (e.g., U.S. Pat. No. 4,528,415, U.S. Pat. No. 3,513,218 and U.S. Pat. No. 3,452,115).

Alternatively, the dimerization catalyst may include an organoaluminum compound of the formula $R_nAlX_{3-n}$, wherein R is selected from alkyls, such as butyl, ethyl and methyl, X is selected from halogens, such as chlorine and n is 0, 1 or 2, for example.

The dimerization reaction may be carried out in any reactor type known in the art, such as via a homogenous reaction in a circulating loop reactor. The dimerization may be carried out under moderate conditions, such as temperatures of from 0° C. to 100° C., or from 25° C. to 70° C., or from 35° C. to 55° C. and pressures of from 50 psig to 500 psig, or from 175 psig to 350 psig, or from 230 psig to 315 psig, for example. The residence time may range from 15-60 minutes, for example.

Metathesis processes generally include reacting the metathesis feed stream with ethylene in the presence of a metathesis catalyst to form a metathesis product stream. As used herein, the term "metathesis" refers to an equilibrium reaction between two olefins where the double bond of each olefin is broken to form intermediate reactants. These intermediates recombine to form new olefin products. In one or more specific embodiments discussed herein, the two olefins include ethylene and butene and the new olefin product is propylene.

As discussed previously herein, butene is fed to the metathesis process via the metathesis feed stream. The ethylene may be fed to the process by methods known to one skilled in the art. For example, the ethylene may be fed to the metathesis process via an inlet separate from an inlet utilized to feed the metathesis feed stream. Alternatively, the ethylene may be combined with the metathesis feed stream prior to the metathesis feed stream passing through such inlet.

The metathesis process includes contacting the butene with ethylene in the presence of a metathesis catalyst. Metathesis catalysts are well known in the art (see, e.g., U.S. Pat. No. 4,513,099 and U.S. Pat. No. 5,120,894). Generally, the metathesis catalyst includes a transition metal oxide, such as transition metal oxides of cobalt, molybdenum, rhenium, tungsten and combinations thereof, for example. In one or more specific embodiments, the metathesis catalyst includes tungsten oxide. The metathesis catalyst may be supported on a carrier, such as silica, alumina, titania, zirconia, zeolites, clays and mixtures thereof, for example. In one or more embodiments, the carrier is selected from silica, alumina and combinations thereof. The catalyst may be supported on a carrier by methods known in the art, such as adsorption, ion-exchange, impregnation or sublimation, for example. The metathesis catalyst may include from 1 wt. % to 30 wt. % or from 5 wt. % to 20 wt. % transition metal oxide, for example.

The metathesis process may further include contacting the butene with ethylene in the presence of an isomerization catalyst (either sequentially or simultaneously with the metathesis catalyst). The isomerization catalyst is generally adapted to convert 1-butene present in the metathesis feed stream to 2-butene for subsequent reaction to propylene. Isomerization catalysts may include zeolites, metal oxides (e.g., magnesium oxide, tungsten oxide, calcium oxide, barium oxide, lithium oxide and combinations thereof), mixed metal oxides (e.g., silica-alumina, zirconia-silica), acidic clays (see, e.g., U.S. Pat. No. 5,153,165; U.S. Pat. No. 4,992,613; U.S. Patent Publication 2004/0249229 and U.S. Patent Publication 2006/0084831) and combinations thereof, for example. In one or more specific embodiments, the catalyst is magnesium oxide. The magnesium oxide may have a surface area of at least 1 m$^2$/g or at least 5 m$^2$/g, for example.

The isomerization catalyst may be supported on a support material, for example. Suitable support materials include silica, alumina, titania, silica-alumina and combinations thereof, for example.

The metathesis processes of the disclosed embodiments include sequentially reacting the metathesis feed stream. In one or more embodiments, the sequential reactions may occur within sequential reaction vessels. In one or more specific embodiments, the sequential reactions occur in a first metathesis reaction by contacting the metathesis feed stream with ethylene in the presence of a first metathesis catalyst and a second metathesis reaction by contacting the at least a portion of the product of the first metathesis reaction with ethylene in the presence of a second metathesis catalyst.

In one or more embodiments, the first metathesis catalyst and the second metathesis catalyst are formed of the same material. Alternatively, in one or more embodiments, the first metathesis catalyst and the second metathesis catalyst are formed of a different material.

In one or more embodiments, ethylene is introduced to the first metathesis reaction and the second metathesis reaction at rates sufficient to provide a lower ethylene:butene molar ratio contacting the first metathesis catalyst than the ethylene:butene ratio contacting the second metathesis catalyst. For example, ethylene may be introduced to the first metathesis reaction at a rate sufficient to provide a first ethylene:butene molar ratio contacting the first metathesis catalyst of from 0.3:1 to 3:1, or from 0.5:1 to 2.5:1, or from 0.75:1 to 2:1. The ethylene may be introduced to the second metathesis reaction at a rate sufficient to provide a second ethylene:butene molar ratio contacting the second metathesis catalyst of from 2.0:1 to 10:1, or from 3.75:1 to 6.75:1, or from 4:1 to 6.5:1, for example.

Advantageously, the sequential processes described herein provide for the ability to tailor each individual metathesis reaction for improved butene conversion (i.e., conversion of butene to propylene). For example, the sequential processes may be tailored such that a lesser feed rate to the second methathesis reaction may be utilized than that utilized to the first metathesis reaction. For example, the sequential processes may exhibit a total butene conversion of at least 80%, or at least 85%, or at least 90%, or at least 95%.

A further advantage of sequential reactors is lower production of higher co-product olefins. These higher olefin co-products are a result of the metathesis reaction of propylene reacting with butylene to produce ethylene and pentene. In the first reactor, a lower ethylene-to-butylene ratio may result in a relatively higher amount of pentenes and higher olefins. The lower ethylene ratio drives the equilibrium towards more of the heavier olefins. These heavy co-products are passed to the second reactor where the higher ethylene-to-butylene ratio converts these co-products back to propylene and butylene, and thus improves the overall selectivity of the process compared to a single-stage reactor.

Further, each metathesis reaction may operate at temperatures and pressures sufficient to provide the feed rates and conversion levels described herein. Accordingly, each reaction temperature and pressure may vary or be the same. However, the metathesis reactions may occur at a pressure of from 150 psig to 600 psig, or from 200 psig to 500 psig, or from 300 psig to 475 psig, for example. The metathesis reactions may occur at a temperature of from 100° C. to 500° C., or from 200° C. to 400° C., or from 300° C. to 350° C., for example. The methathesis reactions may occur at a weight hourly space velocity (WHSV) of from 3 hr$^{-1}$ to 200 hr$^{-1}$, or from 20 hr$^{-1}$ to 40 hr$^{-1}$, for example.

Metathesis product streams generally include a variety of components, including ethylene, propylene, $C_4$ olefins, and $C_{5+}$ olefins (including pentene and hexene, for example). Therefore, metathesis processes often include separation of such components. Methods of separation are known in the art (see, U.S. Pat. No. 7,214,841) and generally include separation within one or more fractionation systems. As used herein, the term "fractionation" refers to processes for the separation of components based on the relative volatility and/or boiling point of the components. The fractionation processes may include those known in the art and the term "fractionation" can be used interchangeably with the terms "distillation" and "fractional distillation" herein.

One or more embodiments described herein include separation after the first metathesis reaction and prior to the second metathesis reaction. For example, the process may include separating at least a portion of the propylene and ethylene from the first metathesis product stream to form a first overhead stream and first de-propenized bottoms stream. It is contemplated that the separation may include a de-propenizer, a de-ethenizer or a combination thereof in any sequence. However, one specific embodiment includes separating the first metathesis product stream within a first de-propenizer (it is contemplated that the first metathesis product stream may be separated within a de-ethenizer prior to separating in the first de-propenizer in an alternative embodiment) to form a first overhead stream including propylene and ethylene and a first de-propenized bottoms stream including butene and $C_{5+}$ olefins. At least a portion of the de-propenized bottoms stream (and in one or more embodiments, all of the de-propenized bottoms stream) is reacted with ethylene via the second metathesis reaction to form the second metathesis product stream.

One or more embodiments further include separation after the second metathesis reaction (either in combination with separation before the second metathesis reaction or exclusive of such separation). For example, the process may include separating at least a portion of the propylene and ethylene from the second metathesis product stream to form a second overhead stream and second de-propenized bottoms stream. It is contemplated that the separation may include a de-propenizer, a de-ethenizer or a combination thereof in any sequence. However, one specific embodiment includes separating the second metathesis product stream within a second de-propenizer (it is contemplated that the second metathesis product stream may be separated within a de-ethenizer prior to separating in the first de-propenizer in an alternative embodiment) to form a second overhead stream including propylene and ethylene and a second de-propenized bottoms stream including butene and $C_{5+}$ olefins.

One or more specific embodiments utilize a de-ethenizer adapted to separate ethylene from the propylene in the first overhead stream and ethylene from the propylene in the second overhead stream to form an ethylene stream and a product propylene stream.

At least a portion of the ethylene stream may be recycled to the first metathesis reaction, the second metathesis reaction or a combination thereof, for example.

It is contemplated that the second de-propenized bottoms stream may undergo further separation. For example, a de-butenizer may receive and separate at least a portion of the second de-propenized bottoms stream to form a recycle butene stream and a de-butenized bottoms stream. The recycle butene stream is composed primarily of the recovered butene and the de-butenized bottoms stream generally includes the $C_{5+}$ olefins.

Referring now to FIG. 1, a simplified process flow diagram of a process 100 for producing propylene according to embodiments disclosed herein is illustrated. FIG. 1 illustrates a process 100 including introducing a metathesis feed stream 102 to a first metathesis reactor 104 having metathesis catalyst 105 (and optional isomerization catalyst—not shown) disposed therein to form metathesis product stream 106 including propylene, ethylene, butene and $C_{5+}$ olefins. FIG. 1 illustrates a specific embodiment wherein ethylene is mixed with the metathesis feed stream 102 via line 108; however, it is contemplated that the ethylene may contact the metathesis feed stream via processes known in the art.

The metathesis product stream 106 is passed to a first de-propenizer 110 to separate at least a portion of the propylene from the metathesis product stream 106 and form a first overhead stream 112 including propylene and ethylene and a first bottoms stream 114 including $C_{4+}$ olefins.

The first bottoms stream 114 is passed to a second metathesis reactor 116 having metathesis catalyst 117 (and optional isomerization catalyst—not shown) disposed therein to form second metathesis product stream 118 including propylene, ethylene, butene and $C_{5+}$ olefins. FIG. 1 illustrates a specific embodiment wherein ethylene is mixed with the second metathesis feed stream 114 via line 120.

The second metathesis product stream 118 is passed to a second de-propenizer 122 to separate at least a portion of the propylene from the second metathesis product stream 118 and form a second overhead stream 124 including propylene and ethylene and a second bottoms stream 126 including $C_{4+}$ olefins.

The first overhead stream 112 and the second overhead stream 124 are mixed via line 128 and introduced to a de-ethenizer 130 to separate at least a portion of the ethylene from the first overhead stream 112 and the second overhead stream 124 and form a propylene product stream 132 and an ethylene stream 134.

While not explicitly illustrated in FIG. 1, optionally, at least a portion of the ethylene stream 134 may be recycled the first metathesis reactor 104, the second metathesis reactor 116 or both the first metathesis reactor 104 and the second metathesis reactor 116.

Those in the art having the benefit of this disclosure will recognize that there are a number of suitable separation techniques well known to the art that may be used to achieve this separation. Any such suitable technique may be used.

EXAMPLES

To facilitate a better understanding of the present invention, the following examples of embodiments are given. In no way should the following examples be read to limit, or to define, the scope of the invention.

An Aspen Plus® simulation of a propylene production process was undertaken. The specific process flow follows that of FIG. 1, while the conditions/rates are shown in Table 1. The rates in Table 1 are based on 100 lbs/hr of Raffinate-II, and ethylene to butene molar ratio of 2.0 in reactor 1 and 6.6 in reactor 2 and a butene conversion of 68% in reactor 1 and 77% in reactor 2. It was observed that the total butene conversion was 92.4% and the total reaction feed was 303 lbs.

TABLE 1

| | (lbs/hr) | | | |
|---|---|---|---|---|
| | Feed Reactor 1 (R1) | Effluent R1 | Feed R2 | Effluent R2 |
| Ethylene | 66.3 | 46.5 | 70.8 | 60.2 |
| Propylene | 2.4 | 63.9 | 5.6 | 35.2 |
| Butenes | 69.3 | 23.8 | 23.8 | 7.7 |
| Butanes | 30.7 | 30.7 | 30.7 | 30.7 |
| Gasoline | 0.0 | 3.6 | 3.6 | 0.6 |
| TOTAL | 168.7 | 168.7 | 134.6 | 134.6 |

A conventional process which has only one metathesis reactor cannot achieve a total butene conversion of 92.4% unless a significant percentage of the de-butenizer overhead stream is recycled. This approach is inefficient since the stream contains an appreciable amount of butanes, which are inert in the metathesis reaction. This is illustrated in Table 2, which is based on 100 lbs/hr of fresh Raffinate-II feed, an ethylene to butene molar ratio of 2.0 in the reactor, and a one-pass butene conversion of 68%. Approximately 82% of the de-butenizer overhead must be recycled to obtain a total butene conversion of 92.4%. The total reactor feed is, as a result, 361 lbs/hr.

TABLE 2

| 1-Pass Conversion (%) | De-butenizer Overhead Stream Recycle (%) | Total Feed (based on 100 lbs/hr of fresh Raff-II) | Overall Conversion (%) |
|---|---|---|---|
| 68 | 0 | 167 | 68.4 |
| 68 | 10 | 175 | 70.6 |
| 68 | 25 | 190 | 74.3 |
| 68 | 50 | 225 | 81.2 |
| 68 | 75 | 306 | 89.7 |
| 68 | 82 | 361 | 92.4 |

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A process for forming propylene comprising:
reacting a metathesis feed stream comprising butene with ethylene in the presence of a first metathesis catalyst via a first metathesis reaction to form a first metathesis product stream comprising propylene, ethylene, butene, and $C_{5+}$ olefins, wherein the first metathesis reaction takes place at an first ethylene to butene molar ratio of 2.0;
separating at least a portion of the propylene and ethylene from the first metathesis product stream to form a first overhead stream and to form a first de-propenized bottoms stream comprising butene and $C_{5+}$ olefins;
reacting at least a portion of the first de-propenized bottoms stream with ethylene in the presence of a second metathesis catalyst via a second metathesis reaction to form a second metathesis product stream comprising propylene, ethylene, butene, and $C_{5+}$ olefins, wherein the second metathesis reaction takes place at an second ethylene to butene molar ratio of 6.6; and
separating at least a portion of the propylene and ethylene from the second metathesis product stream to form a second overhead stream; and
recovering propylene from the first overhead stream, the second overhead stream or combinations thereof.

2. The process of claim 1 further, wherein the first overhead stream comprises propylene and ethylene and the second overhead stream comprises propylene and ethylene.

3. The process of claim 1 further comprising:
separating at least a portion of the first overhead stream to form an ethylene stream and a propylene stream.

4. The process of claim 1 further comprising:
separating at least a portion of the second overhead stream to form an ethylene stream and a propylene stream.

5. The process of claim 1 further comprising:
separating at least a portion of the first overhead stream and at least a portion of the second overhead stream to form an ethylene stream and a propylene stream.

6. The process of claim 5 further comprising recycling at least a portion of the ethylene stream to the first metathesis reaction, the second metathesis reaction or a combination thereof.

7. The process of claim 1, wherein the metathesis feed stream further comprises Raffinate-2 which includes predominantly 1-butene, 2-butene and butanes.

8. The process of claim 1, wherein the first metathesis reaction, the second metathesis reaction or a combination thereof further comprises reacting the corresponding metathesis feed stream with ethylene in the presence of an isomerization catalyst.

9. The process of claim 8, wherein the isomerization catalyst comprises magnesium oxide.

10. The process of claim 1, wherein ethylene is introduced to the first metathesis reaction and the second metathesis reaction at rates sufficient to to make the first ethylene to butene molar ratio is smaller than the second ethylene to butene molar ratio.

11. The process of claim 1, wherein the process exhibits a total butene conversion of at least 85%.

12. The process of claim 1, wherein the first metathesis catalyst and the second metathesis catalyst comprise a transition metal oxide.

13. The process of claim 1, wherein the first metathesis catalyst and second metathesis catalyst comprise the same material.

14. The process of claim 1, wherein separating at least a portion of the propylene and ethylene from the second metathesis product forms a second de-propenized bottoms stream comprising butene and $C_{5+}$ olefins.

* * * * *